(12) United States Patent
Nardi et al.

(10) Patent No.: US 9,006,424 B2
(45) Date of Patent: Apr. 14, 2015

(54) PROCESS FOR THE MANUFACTURE OF IVABRADINE AND OF INTERMEDIATES OF SYNTHESIS THEREOF

(75) Inventors: Antonio Nardi, Segrate (IT); Bruno De Angelis, Segrate (IT); Paolangelo Cerea, Segrate (IT); Jane Llorenc Rafecas, Llorenç del Penedès (ES); Nicolas Tesson, L'Hospitalet de Llobregat (ES)

(73) Assignee: Laboratorio Chimico Internazionale S.p.A., Milan (IT)

( * ) Notice: Subject to any disclaimer, the term of this patent is extended or adjusted under 35 U.S.C. 154(b) by 0 days.

(21) Appl. No.: 14/236,139

(22) PCT Filed: Jul. 31, 2012

(86) PCT No.: PCT/IB2012/001477
§ 371 (c)(1),
(2), (4) Date: Aug. 5, 2014

(87) PCT Pub. No.: WO2013/017937
PCT Pub. Date: Feb. 7, 2013

(65) Prior Publication Data
US 2014/0357859 A1  Dec. 4, 2014

(30) Foreign Application Priority Data
Aug. 1, 2011  (IT) .............. MI2011A1467

(51) Int. Cl.
C07D 223/16 (2006.01)
C07C 213/10 (2006.01)
C07C 215/50 (2006.01)
C07C 57/30 (2006.01)
C07C 53/134 (2006.01)
C07C 209/46 (2006.01)
C07C 211/04 (2006.01)

(52) U.S. Cl.
CPC ............ C07D 223/16 (2013.01); C07C 213/10 (2013.01); C07C 215/50 (2013.01); *C07C 2102/06* (2013.01); C07C 57/30 (2013.01); C07C 53/134 (2013.01); C07C 209/46 (2013.01); C07C 211/04 (2013.01)

(58) Field of Classification Search
USPC ........................................ 540/523
See application file for complete search history.

(56) References Cited

FOREIGN PATENT DOCUMENTS

| EP | 0 534 859 | 3/1993 |
|---|---|---|
| EP | 1 598 333 | 11/2005 |
| WO | WO 2008/070909 | 6/2008 |
| WO | WO 2010/072409 | 7/2010 |

OTHER PUBLICATIONS

International Search Report for PCT/IB2012/001477, mailed Nov. 30, 2012.
Written Opinion of the International Searching Authority for PCT/IB2012/001477, mailed Nov. 30, 2012.
Italy Search Report for Italy Application MI20111467, dated Jan. 12, 2012.

*Primary Examiner* — Bruck Kifle
(74) *Attorney, Agent, or Firm* — Nixon & Vanderhye P.C.

(57) ABSTRACT

The invention concerns a new process for the resolution of ivabradine and of intermediates of synthesis thereof.

8 Claims, 4 Drawing Sheets

PROCESS FOR THE MANUFACTURE OF IVABRADINE AND OF INTERMEDIATES OF SYNTHESIS THEREOF

This application is the U.S. national phase of International Application No. PCT/IB2012/001477, filed 31 Jul. 2012, which designated the U.S. and claims priority to Italy Application No. MI2011A001467, filed 1 Aug. 2011, the entire contents of each of which are hereby incorporated by reference.

SUMMARY OF THE INVENTION

The present invention concerns a new process for the manufacture of ivabradine and of intermediates of synthesis thereof, in particular a new process for resolution of the corresponding racemic mixtures of said compounds.

TECHNICAL BACKGROUND

Ivabradine or 3-[3-({[(7S)-3,4-dimethoxybicyclo[4.2.0]octa-1,3,5-trien-7-yl]methyl}(methy)amino)propyl]-7,8-dimethoxy-1,3,4,5-tetrahydro-2H-3-benzazepine-2-one has the formula (I)

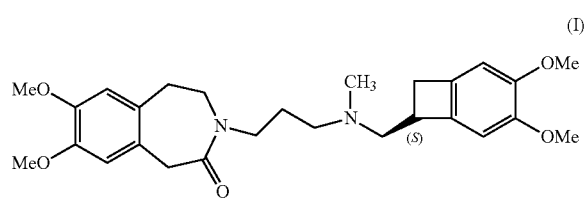

and is used in cardiology for heart failure, hypertension, angina and post-infarction treatment.

Ivabradine is therefore in an enantiomeric form, in particular in the (S) form. The most common synthesis of ivabradine entails condensation between the compounds (II) and (III) shown in the following diagram:

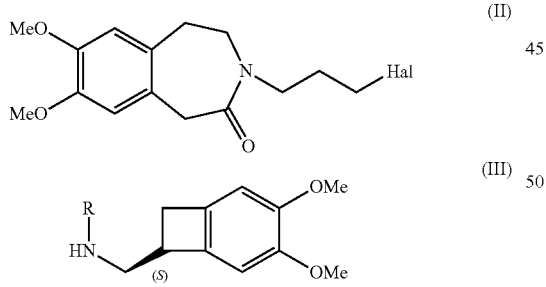

in which R is hydrogen or methyl and Hal is an atom of halogen.

Preparation of the intermediate amine (III) in enantiomerically pure form is the subject of numerous patents.

EP 0 534 859 describes preparation of the compound (III) in which R is methyl, by means of a resolution with camphorsulphonic acid with a yield of 2-3% while EP 1 598 333 describes resolution of the compound (III) in which R is hydrogen with N-acetyl-L-glutamic acid, obtaining better yields. Although said process produces good yields, it must be performed controlling the operating conditions accurately and carefully both during its use as a resolving agent and during its recovery and re-use, since the N-acetyl-L-glutamic acid can give rise to intramolecular reactions, degrading and therefore no longer being available as a reagent for the resolution.

OBJECTS OF THE INVENTION

The object of the present invention is to provide a new process for the resolution of ivabradine or of its intermediates of formula (III) which is industrially applicable, and easy to be performed and cost effective.

Another object of the present invention is to provide a new process for the resolution of ivabradine or its intermediates of formula (III) which allows a simple recycling of the resolution reagent.

DESCRIPTION OF THE INVENTION

According to one of its aspects, the invention concerns a process for the preparation of a compound of formula (A) in the (S) form

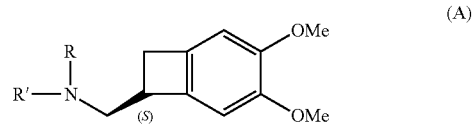

in which R is hydrogen or methyl and R' is hydrogen or a group of formula (IV)

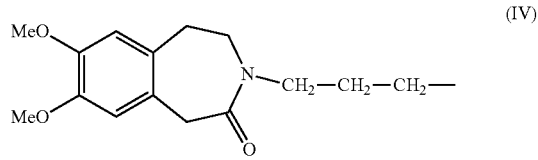 [SMILES: CCCCN1CCc2cc(OC)c(OC)cc2CC1=O]

which comprises
(i) reacting a compound of formula (A) in racemic form with (S)-ibuprofen, in an organic solvent;
(ii) stirring the solution at ambient temperature until a precipitate is obtained;
(iii) treating the precipitate formed in step (ii) with a base to release the compound (A) in the (S) form; and
(iv) optionally isolating the compound of formula (A) in the (S) form.

The (S)-ibuprofen has the following structural formula

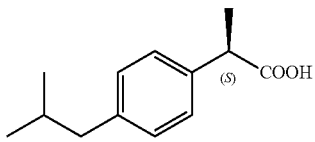

It will be noted that when R is methyl and R' is the group of formula (IV), the molecule A is ivabradine of formula (I).

According to a preferred embodiment, the invention concerns a process as described above in which R' is hydrogen.

According to a particularly preferred embodiment, the invention concerns a process as described above in which R' is hydrogen and R is hydrogen.

Thus, according to a particularly preferred embodiment, the invention concerns a process for the preparation of (1S)-4,5-dimethoxy-1-(ammoniummethyl)-benzocyclobutane of formula (B)

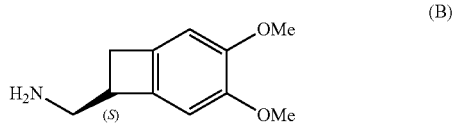

which comprises
(v) reacting the 4,5-dimethoxy-1-(ammoniummethyl)-benzocyclobutane in racemic form with (S)-ibuprofen in an organic solvent;
(vi) stirring the solution at ambient temperature until a precipitate is obtained;
(vii) treating the precipitate formed in step (vi) with a base to release the compound (B) in the (S) form; and
(viii) optionally isolating the compound of formula (B) in the (S) form.

Figure 1:
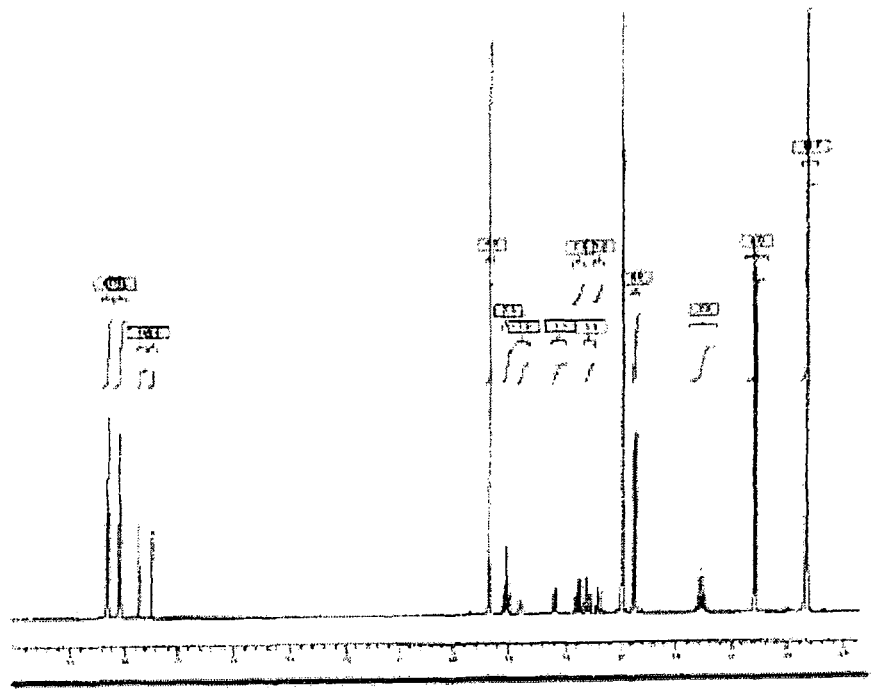
FIG. 1 shows the $^1$H-NMR spectrum of the intermediate (C).

According to the invention, the (S)-ibuprofen is used in an at least equimolar quantity, advantageously in a molar quantity at least double with respect to the racemic starting compounds. According to a preferred embodiment, the (S)-ibuprofen is used in a molar quantity approximately triple that of the racemic starting compounds.

As organic solvent, any organic solvent able to dissolve the racemic starting compounds can be used according to the invention; preferred organic solvents are apolar solvents, for example chosen from among the aromatic hydrocarbons, aliphatic hydrocarbons, acetonitrile and their mixtures.

Suitable solvents include toluene, hexane, heptane, cyclohexane, acetonitrile and their mixtures.

The expression "reacting" here indicates mixing the racemic starting compounds and the (S)-ibuprofen in the chosen organic solvent. The racemic starting compounds and the (S)-ibuprofen can be previously and separately dissolved in the chosen organic solvent.

The reaction between the racemic starting compounds and the (S)-ibuprofen does not require heating and can be performed at ambient temperature. If desired or necessary, the mixture of steps (i) and (v) can also be heated, up to a temperature of approximately 50-60° C., preferably up to 40-50° C., for example around 40-45° C. After mixing it is stirred for a few hours, for example 10-30 hours, advantageously approximately 24 hours, after which the precipitation of a compound occurs.

The compound obtained in steps (ii) or (vi) can be isolated according to the known techniques, for example by filtering.

In steps (iii) or (vii), the compound obtained in steps (ii) or (vi) can be treated with a basic aqueous solution and the desired compound can be obtained by extraction with a water-immiscible organic solvent.

In practice, it is possible to suspend the compound obtained in steps (ii) or (vi) in water, add a base up to basic pH, then extract the compounds (A) or (B) in the (S) form with a water-immiscible organic solvent. The organic solution containing the desired compound can be used as is for any subsequent reactions or the desired compound can be isolated according to the methods known to a person skilled in the art.

The base used in steps (iii) or (vii) can be organic, for example triethylamine, or inorganic, for example sodium bicarbonate, sodium or potassium hydroxide, etc.

The organic solvent can be any water-immiscible organic solvent, for example toluene, ethyl acetate, dichloromethane, etc.

The (S)-ibuprofen remaining in the aqueous phase can be simply recovered and re-used via techniques known to a person skilled in the art such as extraction of the the (S)-ibuprofen with water-immiscible organic solvents or by precipitation and filtering of the (S)-ibuprofen from the aqueous phase after acidification of the solution with strong inorganic acids, for example hydrochloric acid, sulphuric acid, etc., or organic acids, for example trifluoroacetic acid, methanesulphonic acid, p-toluenesulphonic acid, etc.

It has been unexpectedly observed that when a quantity higher than the stoichiometric quantity of (S)-ibuprofen is used (i.e. when the ratio in moles between (S)-ibuprofen and the racemic starting compound (A) or (B) is higher than 1, for example equal to or higher than 2), the precipitate that forms is not a simple salt of the compounds (A) or (B) in the (S) form with the (S)-ibuprofen but is a co-crystal which comprises the compounds (A) or (B) in the (S) form and the (S)-ibuprofen in the proportion 1:2, which contains a molecule of compounds (A) or (B) in the (S) form and two molecules of (S)-ibuprofen.

In particular, the co-crystal is formed of a salt of compounds (A) or (B) in the (S) form and a molecule of (S)-ibuprofen, solvated with a further molecule of (S)-ibuprofen.

Said co-crystal can be isolated according to the known methods, for example by filtering and, if necessary or desired, can be further purified, for example by re-suspension in a solvent and subsequent filtering or crystallisation.

It has been noted that said co-crystal precipitates with good yields and is a stable and easily workable compound. If desired or necessary, the product can be purified, for example by means of one or more crystallisations, to increase the enantiomeric excess.

According to a preferred embodiment, in order to directly obtain the crystal with a good enantiomeric excess, it is expedient to include a small quantity of crystal in pure form in the reaction solution. In this way the desired crystalline compound is obtained with excellent yields and high enantiomeric purity.

The co-crystal formed in step (vi), i.e. the co-crystal formed of a molecule of compound of formula (B) in the (S) form and two molecules of (S)-ibuprofen, was characterised by $^1$H NMR, X ray diffraction, differential scanning calorimetry (DSC) and thermogravimetric analysis (TGA). The results of these characterisations are reported in the experimental section of the present description and in the attached figures.

Said co-crystal, formed as described above in step (vi) reported above and better explained in the experimental section, is therefore composed of the salt formed of a molecule of the compound of formula (B) in the (S) form and a molecule of (S)-ibuprofen, co-crystallised with another molecule of (S)-ibuprofen, and is the compound:
(S)-ibuprofenate of (1S)-4,5-dimethoxy-1-(ammoniummethyl)-benzocyclobutane.(S)-ibuprofen, having the following formula (C)

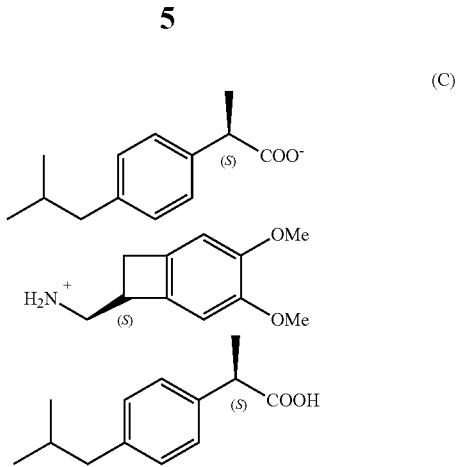

(C)

Figure 2:
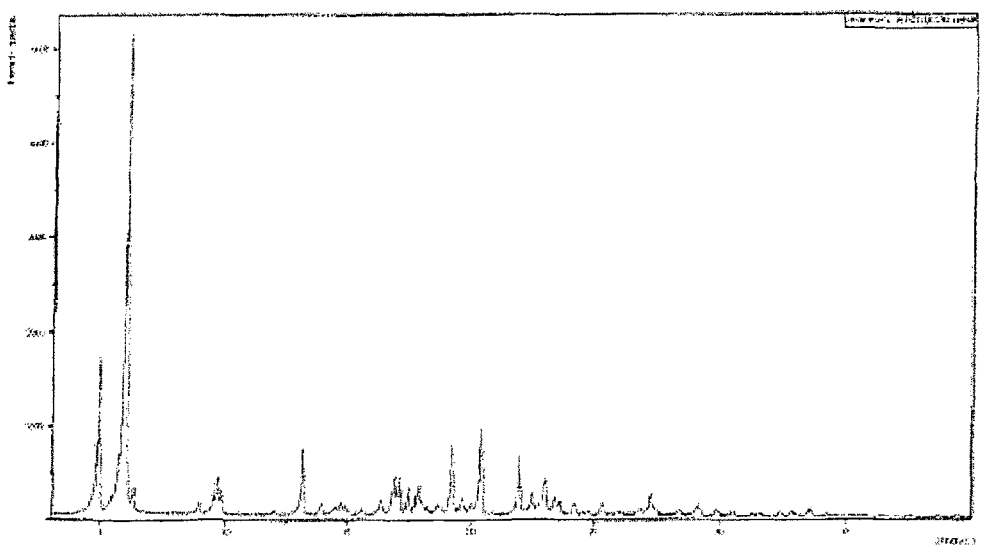
FIG. 2 shows the X ray diffraction spectrum of the intermediate (C).

FIG. 1 shows the $^1$H NMR spectrum of the compound (C) and FIG. 2 shows the X ray powder diffraction (XRPD) spectrum of the compound (C).

The co-crystal of formula (C) is a new compound and constitutes a further subject of the present invention, as does its use for the preparation of a compound chosen from (1S)-4,5-dimethoxy-1-(ammoniummethyl)-benzocyclobutane and ivabradine.

According to another of its embodiments, the invention concerns the use of the compound (B) obtained according to the invention for the preparation of ivabradine. The process of the invention therefore unexpectedly and surprisingly allows, for example, the compound (B) to be obtained using the molecule of the (S)-ibuprofen (which is normally used in therapy as an anti-inflammatory drug, rather than as a resolution agent) with excellent yields and in a simple industrially feasible manner, as also illustrated in the experimental section of the present description.

The invention will now be better described via the following illustrative non-limiting examples.

EXPERIMENTAL SECTION

Proton Nuclear Magnetic Resonance

The $^1$H NMR spectra were recorded in deuterated dimethyl sulphoxide with a Varian Mercury 400 spectrophotometer, equipped with a 5 mm ATB 1H/19F/X broadband probe. The spectra were acquired by dissolving 5-10 mg of sample in 0.6 ml of deuterated solvent.

X Ray Diffraction

The XRPD analysis was performed using a Philips XPert diffractometer with Cu $K_\alpha$ radiations in Bragg-Brentano geometry. The system is equipped with RTMS (Real Time Multiple Strip) multidetector. The diffraction pattern was recorded from 3° to 40° (2θ) at a scanning speed of 17.7° per minute.

DSC

Figure 3:
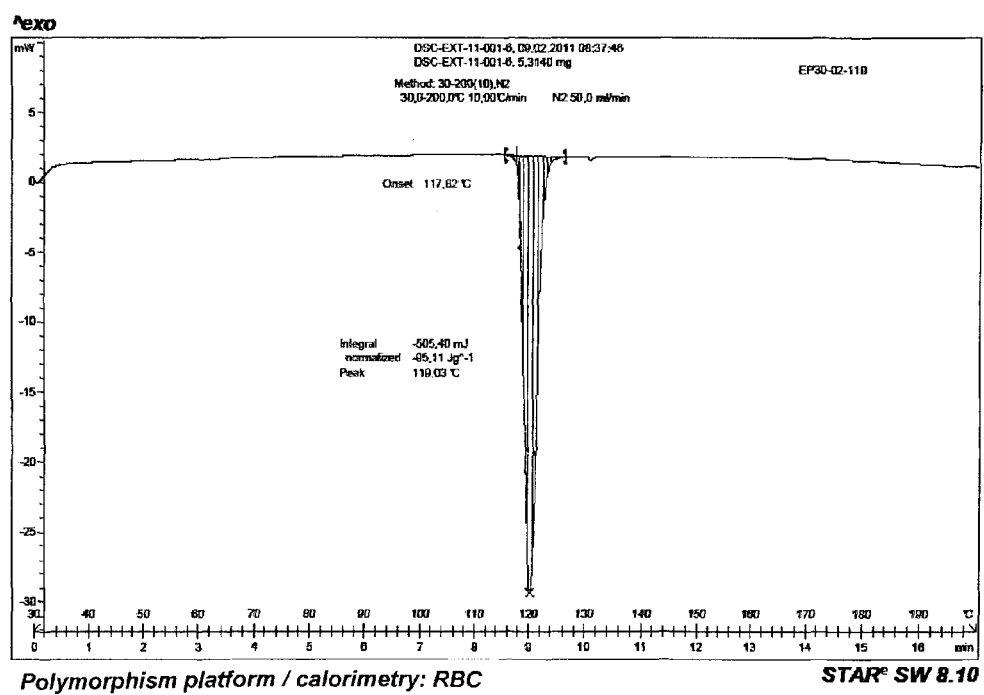
FIG. 3 shows the DSC graph of the intermediate (C).

The DSC analysis was recorded with a Mettler DSC822$^e$. A 5.3140 mg sample was weighed in a 40 microl aluminium crucible with perforated cover and heated under nitrogen (50 ml/min) at 10° C./minute from 30 to 200° C. The endothermic peak corresponding to the melting point begins at 117.82° C. (melting enthalpy—95.11 J/g). The graph is shown in FIG. 3.

TGA

Figure 4:
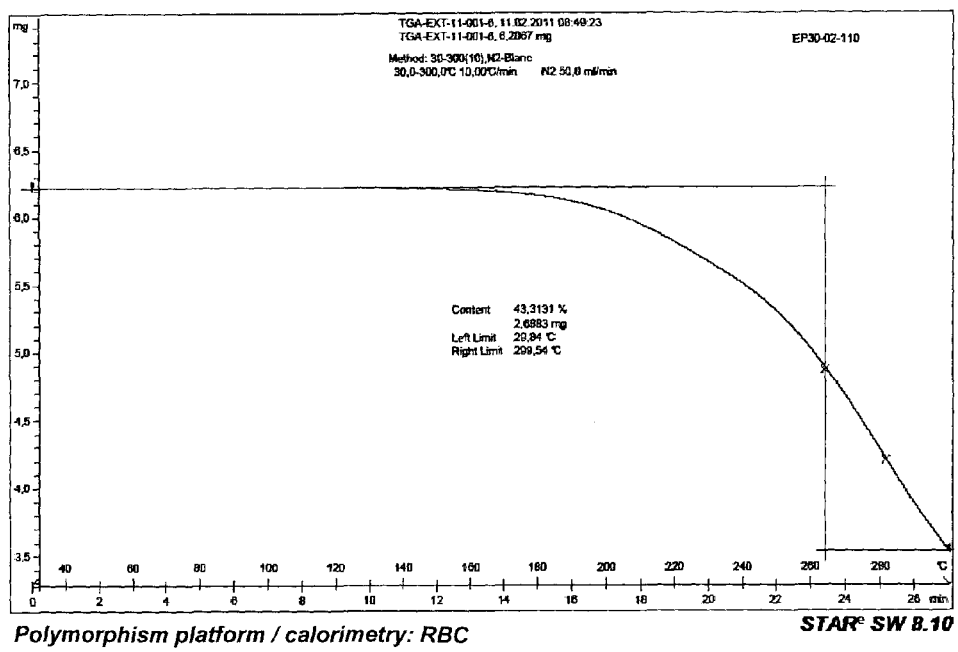
FIG. 4 shows the TGA graph of the intermediate (C).

The thermogravimetric analysis was recorded in a Mettler TGA/SDTA851$^e$ thermogravimetric analyser. A sample of 6.2067 mg was weighed in a 70 microl aluminium crucible with perforated cover and heated under nitrogen (50 ml/min) at 10° C./minute from 30 to 200° C. The analysis did not show loss of water at temperatures below the melting point. The graph is shown in FIG. 4.

Chiral High Performance Liquid Chromatography (Chiral HPLC)

Direct Analysis of the Co-Crystal

The samples were prepared by dissolving the co-crystal in methanol (2 mg/ml). The enantiomeric excess (e.e.) was measured with Agilent Technologies HP1100 apparatus equipped with UV/vis photodiode array detector. Ethanol containing 0.1% diethylamine at a flow speed of 0.4 ml/minute through a Chiralpack IA column was used as the mobile phase. The samples were analysed at 220 nm:

Rt=12.1 min (1R)-4,5-dimethoxy-1-(ammoniummethyl)-benzocyclobutane

Rt=12.3 min (1S)-4,5-dimethoxy-1-(ammoniummethyl)-benzocyclobutane (Compound (B))

Analysis of (1R) and derivatized (1S)-4,5-dimethoxy-1-(ammoniummethyl)-benzocyclobutane The co-crystal was treated with a biphasic mixture of dichloromethane and aqueous NaOH. The aqueous phase was extracted with dichloromethane and the reunited organic extracts were dry-evaporated. The derivatization of the compound was performed by reaction with methyl chloroformate in toluene-methanol-water in the presence of sodium bicarbonate.

The samples were prepared by dissolving a compound derivatized in heptane: isopropyl alcohol (95:5.2 mg/ml). The enantiomeric excess (e.e.) was measured with Agilent Technologies HP 1100 apparatus equipped with UV/vis photodiode array detector. Heptane:IPA (95:5) at a flow speed of 0.4 ml/minute through a Chiralpack IA column was used as the mobile phase. The samples were analysed at 220 nm:

Rt=16.2 min derivatized (1R)-4,5-dimethoxy-1-(ammoniummethyl)-benzocyclobutane

Rt=20.3 min derivatized (1S)-4,5-dimethoxy-1-(ammoniummethyl)-benzocyclobutane (Compound (B)).

Example 1

Preparation of (S)-ibuprofenate of (1S)-4,5-dimethoxy-1-(ammoniummethyl)-benzocyclobutane. (S)-ibuprofen Example 1a Preparation of the Title Compound A solution of 5.65 g (29.2 mmoles) of 4,5-dimethoxy-1-(ammoniummethyl)-benzocyclobutane racemate in 30 ml of acetonitrile is added at ambient temperature, in 25 minutes, to a 100 ml three-necked flask with mechanical stirrer, metering funnel and thermometer, containing 18.12 g (87.8 mmoles) of S-ibuprofen dissolved in 27 ml of acetonitrile. A slight exothermic reaction is noted during the addition. At the end, the mixture is stirred for 24 hours at ambient temperature, after which the resulting precipitate is filtered, washed with acetonitrile and dried in a vacuum at ambient temperature to obtain the title compound as a white solid (7.12 g, yield 40%).

Example 1b

Crystallization 1 g (1.65 mmoles) of the compound obtained in example 1a is dissolved in 6 ml of acetonitrile by heating in a bath at 58° C. The solution is then stirred at ambient temperature for 18 hours. The resulting solid is filtered and washed with acetonitrile, then dried in a vacuum at ambient temperature to give the title compound. The crystallization is repeated until the title compound is obtained with an e.e. of 98.0% HPLC.

Example 2

Preparation of (S)-ibuprofenate of (1S)-4,5-dimethoxy-1-(ammoniummethyl)-benzocyclobutane. (S)-ibuprofen The procedure is the same as in Example 1a, but after stirring the mixture for 19 hours, instead of 24 hours, it is heated to 42° C. (internal) for one hour, seeded with a crystal of the title compound and then stirred for 4 hours at ambient temperature. In this way the title compound is obtained as a white solid with yield of 38% (e.e. 86.6% HPLC).

Example 3

Preparation of (S)-ibuprofenate of (1S)-4,5-dimethoxy-1-(ammoniummethyl)-benzocyclobutane. (S)-ibuprofen

Example 3a 4.35 g (21.1 mmoles) of (S)-ibuprofen are added, at ambient temperature, to a 100 ml three-necked flask with mechanical stirrer and thermometer, containing a suspension of 1.36 g (7.04 mmoles) of 4,5-dimethoxy-1-(ammoniummethyl)-benzocyclobutane racemate in cyclohexane, and seeded with a crystal of the title compound. The mixture is stirred for 24 hours at ambient temperature, after which the resulting precipitate is filtered, washed with cyclohexane and dried in a vacuum at ambient temperature to obtain the title compound as a white solid (1.82 g, yield 43%, e.e. 74.6% HPLC).

Example 3b

The compound thus obtained is purified by re-suspension in acetonitrile, stirring for 24 hours, and subsequent filtering to obtain the title compound as a white solid (e.e. 96.6% HPLC).

$^1$H NMR (dmso, 400 MHz): d=7.18-7.13 (m, 4H); 7.07-7.02 (m, 4H); 6.86 (s, 1H); 6.75 (s, 1H); 3.67 (s, 6H); 3.52 (q, J=7.0 Hz, 2H); 3.44-3.36 (m, 1H); 3.09 (dd, J=4.7 Hz, J=13.7 Hz, 1H); 2.89 (dd, J=6.6 Hz, J=12.5 Hz, 1H); 2.80 (dd, J=7.8 Hz, J=12.5 Hz, 1H); 2.70 (dd, J=1.9 Hz, J=13.7 Hz, 1H); 2.38 (d, J=7.0 Hz, 4H); 1.84-1.71 (m, 2H); 1.29 (d, J=7.0 Hz, 6H); 0.83 (d, J=6.6 Hz, 12H) (FIG. 1).

X ray diffraction, peaks with intensity equal to or higher than 1%

| Position [°2Th.] | d-spacing [Å] | Relative intensity [%] |
|---|---|---|
| 4.95 | 17.84 | 33 |
| 6.06 | 14.59 | 100 |
| 6.40 | 13.81 | 5 |
| 8.98 | 9.85 | 2 |
| 9.70 | 9.12 | 7 |
| 9.88 | 8.95 | 4 |
| 12.7 | 7.33 | 1 |
| 13.21 | 6.70 | 13 |
| 14.00 | 6.32 | 3 |
| 14.52 | 6.10 | 2 |
| 14.79 | 5.99 | 3 |
| 14.96 | 5.92 | 2 |
| 15.64 | 5.67 | 1 |
| 16.38 | 5.41 | 3 |
| 16.91 | 5.24 | 8 |
| 17.13 | 5.18 | 7 |
| 17.49 | 5.07 | 5 |
| 17.84 | 4.97 | 5 |
| 18.63 | 4.76 | 1 |
| 19.20 | 4.62 | 14 |
| 19.61 | 4.53 | 3 |
| 20.00 | 4.44 | 2 |
| 20.38 | 4.36 | 18 |
| 21.99 | 4.04 | 12 |
| 22.51 | 3.95 | 4 |
| 23.00 | 3.86 | 6 |
| 23.08 | 3.85 | 7 |
| 23.48 | 3.79 | 4 |
| 23.67 | 3.76 | 2 |
| 24.24 | 3.67 | 3 |
| 25.37 | 3.51 | 2 |
| 26.85 | 3.32 | 1 |
| 27.25 | 3.27 | 5 |
| 28.42 | 3.14 | 1 |
| 29.13 | 3.07 | 2 |
| 29.83 | 2.99 | 1 |
| 33.55 | 2.67 | 1 |

Example 5

Preparation of (1S)-4,5-dimethoxy-1-(ammoniummethyl)-benzocyclobutane

An aqueous solution of 10% sodium hydroxide is added to a suspension of 1.00 g (5.18 mmoles) of (1S)-4,5-dimethoxy-1-(ammoniummethyl)-benzocyclobutane in 10 ml of water up to pH 8. Ethyl acetate is then extracted (3×10 ml). The reunited organic phases are dried on sodium sulphate and the solvent is evaporated in a vacuum. In this way 0.30 g of title compound are obtained.

The invention claimed is:

1. Process for the preparation of a compound of formula (A) in its (S) form

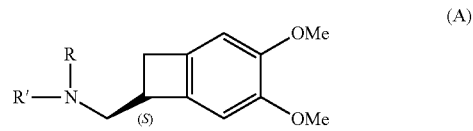

(A)

wherein R is hydrogen or methyl and R' is hydrogen or a group of formula (IV)

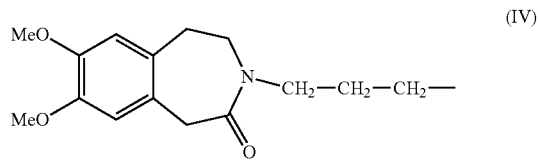 [SMILES: CCCCN1CCc2cc(OC)c(OC)cc2CC1=O]

(IV)

which comprises
(i) reacting a compound of formula (A) in racemic form with (S)-ibuprofen, in an organic solvent;
(ii) stirring the solution at room temperature until a precipitate occurs;
(iii) treating the precipitate formed in step (ii) with a base to release compound (A) in its (S) form; and (iv) optionally isolating the compound of formula (A) in its (S) form.

2. Process according to claim 1 wherein R' is hydrogen.

3. Process according to claim 1, wherein R' is hydrogen and R is hydrogen, for the preparation of (1S)-4,5-dimethoxy-1-(ammoniummethyl)-benzocyclobutane of formula (B)

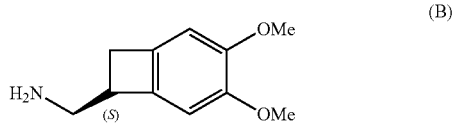

(B)

which comprises:
(v) reacting racemic 4,5-dimethoxy-1-(ammoniummethyl)-benzocyclobutane with (s)-ibuprofen in an organic solvent;
(vi) stirring the solution at room temperature until a precipitate occurs;
(vii) treating the precipitate formed in step (vi) with a base to release compound (B) in its (S) form; and
(viii) optionally isolating compound of formula (B) in its (S) form.

4. Process according to claim 1, wherein (S)-ibuprofen is used in an at least double amount with respect to the racemic starting compounds.

5. Process according to claim 4, wherein (S)-ibuprofen is used in an at least triple amount with respect to the racemic starting compounds.

6. Process according to claim 1, wherein said organic solvent is selected from acetonitrile and cyclohexane.

7. Process according to claim 1, wherein the precipitate formed in steps (ii) and (vi) is treated with an aqueous basic solution and extracted with a water immiscible organic solvent.

8. (S)-ibuprofenate of (1S)-4,5-dimethoxy-1-(ammoniummethyl)-benzocyclobutane.(S)-ibuprofen having the following formula (C)

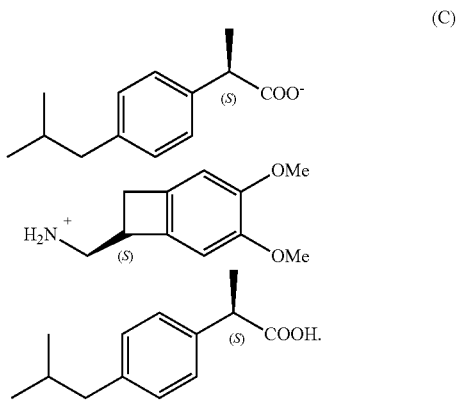

(C)

* * * * *